(12) United States Patent
Wolleschensky et al.

(10) Patent No.: US 7,688,442 B2
(45) Date of Patent: Mar. 30, 2010

(54) METHOD TO BE USED IN FLUORESCENCE MICROSCOPY

(75) Inventors: Ralf Wolleschensky, Apolda (DE);
Bernhard Zimmermann, Jena (DE);
Richard Ankerhold, Freising (DE)

(73) Assignee: Carl Zeiss Microimaging GmbH, Jena (DE)

( * ) Notice: Subject to any disclaimer, the term of this patent is extended or adjusted under 35 U.S.C. 154(b) by 683 days.

(21) Appl. No.: 10/560,426

(22) PCT Filed: Jun. 9, 2004

(86) PCT No.: PCT/EP2004/006202

§ 371 (c)(1),
(2), (4) Date: Mar. 16, 2007

(87) PCT Pub. No.: WO2004/113987

PCT Pub. Date: Dec. 29, 2004

(65) Prior Publication Data

US 2007/0178602 A1 Aug. 2, 2007

(30) Foreign Application Priority Data

Jul. 16, 2003 (DE) .................................. 103 27 382

(51) Int. Cl.
*G01N 21/64* (2006.01)
(52) U.S. Cl. .................... 356/318; 250/458.1
(58) Field of Classification Search .................. 356/317, 356/318
See application file for complete search history.

(56) References Cited

U.S. PATENT DOCUMENTS

| 6,167,173 | A | 12/2000 | Schoeppe et al. |
| 6,602,716 | B1 | 8/2003 | Klimant |
| 7,009,699 | B2 | 3/2006 | Wolleschensky et al. |

FOREIGN PATENT DOCUMENTS

| DE | 198 29 657 | A1 | 2/1999 |
| DE | 19829657 | A1 | 2/1999 |
| DE | 199 00 135 | A1 | 8/1999 |
| DE | 19900135 | A1 | 8/1999 |
| DE | 199 15 137 | A1 | 10/2000 |
| DE | 19915137 | A1 | 10/2000 |
| EP | 1 308 715 | A1 | 5/2003 |
| EP | 1308715 | A1 | 5/2003 |
| GB | 2 333 153 | A | 7/1999 |
| GB | 2333153 | A | 7/1999 |

OTHER PUBLICATIONS

Lansford, et al., "Resolution of Multiple Green Fluorescent Protein Color Variants and Dyes Using Two-Photon Microscopy and Imaging Spectroscopy", Journal of Biomedical Optics, SPIE, vol. 6, No. 3, pp. 311-318, Jul. 2001.
Ando, et al., "An Optical Marker Based on the UV-induced Green-to-Red Photoconversion of a Fluorescent Protein", PNAS, vol. 99, No. 20, pp. 12651-12656, Oct. 1, 2002.
Patterson, et al., "A Photoactivatable GFP for Selective Photolabeling of Proteins and Cells", Science, vol. 297, No. 5588, pp. 1873-1877, Sep. 13, 2002 (Abstract Only).
Lansford et al.; "Resolution of Mulitple Green Fluorescent Protein Color Variants and Dyes using Two-Photon Microscopy and Imaging Spectroscopy"; *Journal of Biomedical Optics*; Jul. 2001; pp. 311-318; vol. 6, No. 3; SPIE Publications, USA.
Ando et al.; "An Optical Marker Based on the UV-Induced Green-to-Red Photoconversion of a Fluorescent Protein"; *Proceedings of the National Acadamy of Sciences of the United States of America*; Sep. 2002; pp. 12651-12656; vol. 99, No. 2; National Academy of Sciences; USA.
Patterson et al.; "A Photoactivatable GFP for Selective Photolabeling of Proteins and Cells"; *Science*; Sep. 2002; pp. 1873-1877; vol. 297, No. 5588; National Institutes of Health; USA.

*Primary Examiner*—F. L Evans
(74) *Attorney, Agent, or Firm*—Jacobson Holman PLLC

(57) ABSTRACT

A method using fluorescence microscopy for image evaluation using a laser scanning microscope in which an at least partially spectrally resolved detection of the fluorescence spectrum occurs. Reference spectra are used for spectral demixing. Temporally and/or spectrally variable dyes and/or dye combinations are employed for recording of the reference spectra. Finally, the recorded reference spectra are inspected for image evaluation.

12 Claims, 5 Drawing Sheets

Detector unit/optics structure

METHOD TO BE USED IN FLUORESCENCE MICROSCOPY

CROSS-REFERENCE TO RELATED APPLICATIONS

The present patent application is a nationalization of International Application No. PCT/EP2004/006202, filed Jun. 9, 2004, which is based on, and claims priority from, German Application No. DE 103 27 382, filed Jun. 16, 2003, both of which are incorporated herein by reference in their entireties.

BACKGROUND OF THE INVENTION

1. Field of the Invention

The invention relates to a method used in fluorescence microscopy, especially laser scanning microscopy, in general, and to the use of dyes for image evaluation, in particular.

2. Description of Related Art

A conventional application of light microscopy for investigation of biological preparations is fluorescence microscopy which is discussed in the "Handbook of Biological Confocal Microscopy, Second Edition", Pawley, Plenum Press, 1995. Specific dyes are used in fluorescence microscopy for specific marking of tissues, cells, cell parts, or other materials.

The emitted photons of a specific energy excite the dye molecules from the ground state to an excited state by absorption of a photon. This excitation is generally referred to as one-photon absorption (See FIG. 1$a$). The dye molecules so excited can return in different ways to the ground state. In fluorescence microscopy the transition with emission of a fluorescence photon is most important. The wavelength of the emitted photon is generally red-shifted based on the Stokes Shift in comparison to the excitation radiation and therefore has a greater wavelength. The Stokes Shift permits separation of the fluorescence radiation from the excitation radiation.

A multiphoton excitation is shown in FIG. 1$b$. The fluorescence light is split and observed separately from the excitation radiation with appropriate dichroic beam splitters in combination with block filters. The depiction of individual cell parts stained with different dyes is possible on this account. However, several parts of a preparation, in principle, can also be simultaneously stained with different dyes by specifically adding dyes resulting in multiple fluorescence. Special dichroic beam splitters are again used to distinguish the fluorescence signals emitted by the individual dyes.

The prior art is explained as follows based on the example of a confocal laser scanning microscope (LSM) such as that show schematically in FIG. 2. An LSM is divided into essentially four modules: light source L, scan module S, detection unit D and microscope M. These modules are further described below. U.S. Pat. No. 6,167,173 also provides a detailed explanation of the LSM and is incorporated by reference herein as if reproduced in its entirety.

For specific excitation of different dyes in one preparation, different wavelengths are used in an LSM laser. The choice of excitation wavelength is guided according to the absorption properties of the dyes being investigated. The excitation radiation is generated in the light source module L. Different lasers 13.1 and 13.2 are used here (for example, argon, argon-krypton, TiSa lasers). Selection of the wavelength and adjustment of the intensity of the required excitation wavelength additionally occurs in the light source module L, for example by using an acousto-optic crystal 15.1 and 15.2. The laser radiation then goes to the scan module S via a fiber 14.1 and 14.2 and/or appropriate mirror arrangement.

The laser radiation generated in the light source is focused into the preparation with limited diffraction with objective 4 via the scanner 23, scan optics 16 and 17 and tube lens 9. The focus scans the sample in the x-y direction point-like. The pixel residence times during scanning over the sample are generally in the range of less than a microsecond to a few seconds.

During confocal detection (descanned detection) of the fluorescence light, the light emitted from the focal plane (specimen) 5 and from the overlying and underlying planes goes to a dichroic beam splitter (MDB) 24 via the scanner 23. This separates the fluorescence light from the excitation light. The fluorescence light is then focused on a diaphragm (confocal diaphragm/pinhole) 29, which is situated precisely in a plane conjugated to the focal plane. Fluorescence light fractions outside of the focus are suppressed on this account. By varying the diaphragm size the optical resolution of the microscope can be adjusted. Behind the diaphragm there is an additional dichroic block filter (EF) 30 that again suppresses the excitation radiation. After passing through the block filter, the fluorescence light is measured by means of a point detector (PMT) 31.

During use of multiphoton absorption, excitation of dye fluorescence occurs in a small volume on which the excitation intensity is particularly high. This region is only slightly larger than the detected region during use of a confocal arrangement. The use of a confocal diaphragm can therefore be omitted and detection can occur directly after the objective 5 in the nondescanned detection region 71 of the microscope.

In another arrangement for detection of dye fluorescence excited by multiphoton absorption, descanned detection again occurs, but this time the pupil of the objective is imaged in the detection unit (nonconfocal descanned detection) D.

Only the plane (optical section) that is situated in the focal plane of the objective is detected by a three-dimensionally illuminated image by both detection arrangements in conjunction with the corresponding one photon or multiphoton absorption. By marking several optical sections in the x-y plane at different depths z of the sample, a three-dimensional image of the sample can then be generated in computer-controlled fashion. The LMS is therefore suitable for investigating thick preparations. The excitation wavelengths are determined by the employed dye with specific absorption properties. Dichroic filters 30 adjusted to the emission properties of the dye ensure that only the fluorescence light emitted by the corresponding dye is measured by the point detector.

In biomedical applications several different cells or cell regions are now marked with different dyes simultaneously (multifluorescence). The individual dyes can be detected separately with the prior art based either on different absorption properties or emission properties (spectra). For this purpose additional splitting of the fluorescence light from several dyes occurs with the secondary beam splitters (DBS) 28 and a separate detection of the individual dye emissions in separate point detectors (PMT x) 31. Flexible adjustment of detection and excitation to corresponding new properties by the user is not possible with the arrangement described above. New dichroic beam splitters and block filters must instead be created for each (new) dye.

If the emission spectra of two dyes overlap, the previous detection devices reach their limits. In order to avoid overlap between two dyes, the spectral detection range must be restricted. The range in which the two dyes overlap is simply cut out for this purpose and not detected. The efficiency of the detection unit therefore deteriorates. An equal signal-to-noise ratio can only be achieved by increasing the excitation power, through which preparation damage can occur. Nowadays a maximum of up to six different dye probes are therefore simultaneously used, since the dyes otherwise could not be separated owing to the strongly overlapping emission bands.

Previously dyes have been modified so that they either differ from each in their absorption properties or in their emission properties. FIG. 3 shows the emission spectra of different typical dyes. The emission signal is plotted as a function of wavelength. The dyes denoted 1 to 4 differ in position and form of their emission spectra. These dyes, however, are in most cases toxic for living preparations. Investigation of the evolution of cell structure in living preparations is therefore impossible. In the late 90s, dyes occurring in nature, the so-called fluorescing proteins (GFP, YFP, CFP, TOPAS, GFT, RFP) were discovered by Clonetech, Mountain View, Calif. www.clontech.com. Fluorescence dyes for specific marking of preparations are used in all of the aforementioned systems.

BRIEF SUMMARY OF THE INVENTION

The present invention covers a method using fluorescence microscopy for image evaluation using a laser scanning microscope in which an at least partially spectrally resolved detection of the fluorescence spectrum occurs. Reference spectra are used for spectral demixing. Temporally and/or spectrally variable dyes and/or dye combinations are employed for recording of the reference spectra. Finally, the recorded reference spectra are inspected for image evaluation.

The inventive method records organic, intracellular, and intercellular processes. Cells and/or cell populations can also be recorded. Reference spectra of photoconvertible dyes, photoactivatable dyes, and indicator dyes can also be recorded.

Of interest to the inventive method is that dyes used in recording reference spectra change their spectra dynamically based on intracellular processes. Also, dyes that have a different rise in fluorescence intensity are used. One fluorescing protein that has been used to practice the present invention is Kaede.

DETAILED DESCRIPTION OF THE INVENTION

Figure 1:
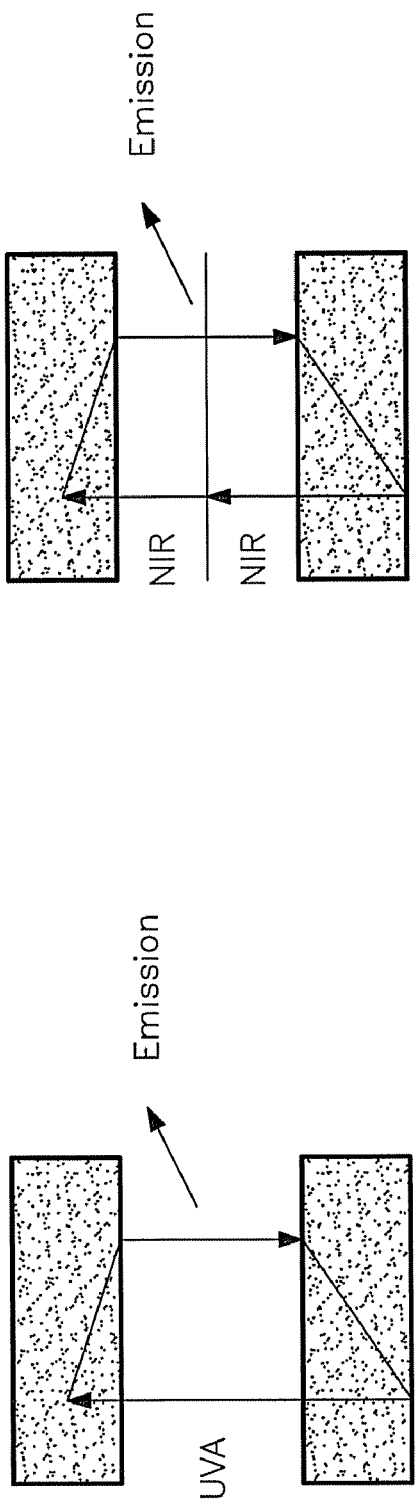
FIG. 1a schematically illustrates the concept of one-photon absorption.
FIG. 1b schematically illustrates the concept of multiphoton absorption.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

Figure 5:
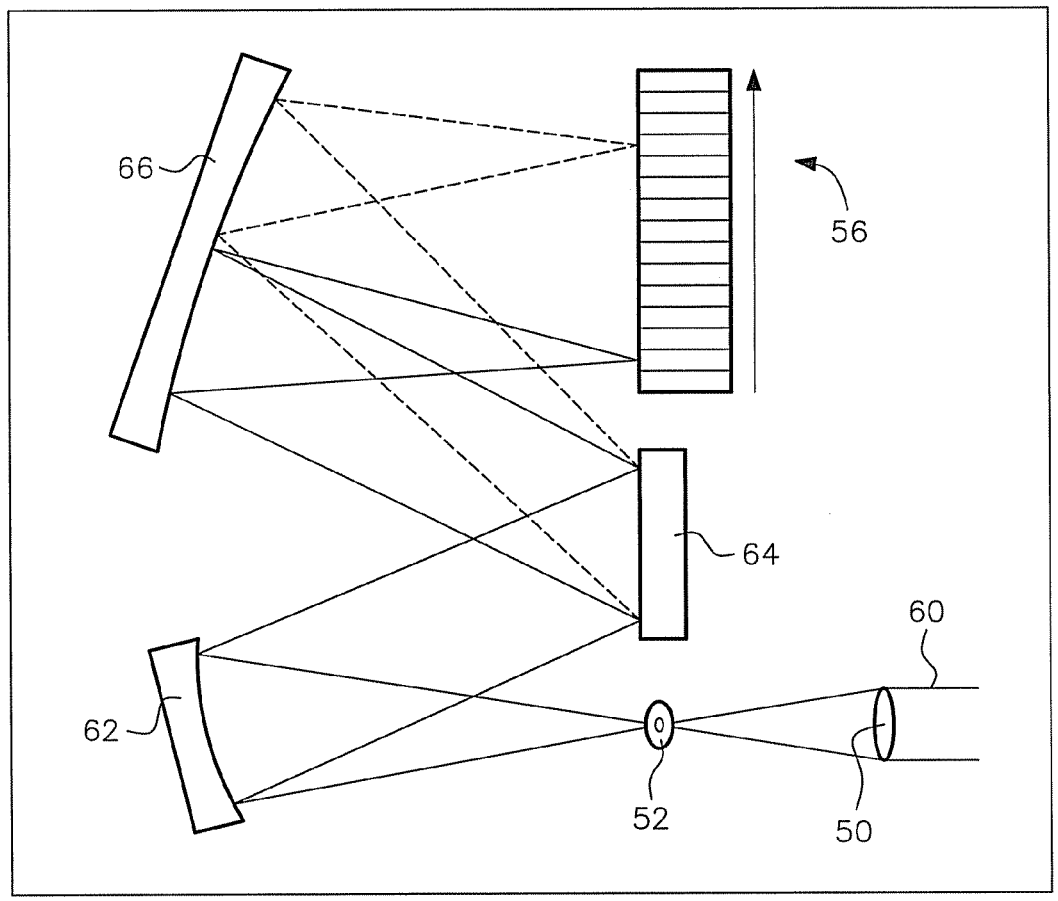
FIG. 5 is a block diagram of the main color divider (MDB) used in practicing the inventive method.

In a laser scanning microscope, such as the Zeiss META, the fluorescence is spit spectrally. For this purpose the emission layer is split from the excitation light in the scan module S of in the microscope (during multiphoton absorption) by means of the main color divider (MDB) 24. A block diagram of a detector unit used in practicing the present invention is shown in FIG. 5.

The light of the sample is focused by means of an imaging optics 50 during confocal detection through an iris (pinhole) 52 so that fluorescence that originated outside of the focus is suppressed. During nondescanned detection the diaphragm drops out. The light is now broken down into its spectral fractions by means of an angle-dispersive element. Prisms, gratings and acousto-optic elements are considered as angle-dispersive elements. The light split by the dispersive element into its spectral components is finally imaged in a line detector 56. This line detector 56 therefore measures the emission signal as a function of wavelength and converts it to electrical signals. In addition, the detection unit can have a line filter (not shown) connected in front to suppress excitation wavelengths.

The depicted structure essentially describes a Cerny-Turner-Design. During confocal detection the light 60 of the sample is focused with the pinhole optics 50 through the confocal diaphragm 52. During a nondescanned detection, in the case of multiphoton absorption, this diaphragm can drop out. The first imaging mirror 62 collimates the fluorescence light. The light then impinges on a line grating 64, for example a grating with a line number of 651 lines per mm. The grating diffracts the light according to its wavelength in different directions. The second imaging mirror 66 focuses the individual spectrally split wavelength fractions onto the corresponding channels of the line detector 56. The use of a line-secondary electron multiplier H7260 made by the Hamamatsu Photonics, K.K., headquartered in Hamamatsu City, Japan (www.hamamatsu.com), is particularly advantageous. The detector has 32 channels and high sensitivity. The free spectral range of the aforementioned variant is about 350 nm. The free spectral range in this arrangement is uniformly distributed in the 32 channels of the line detector so that an optical resolution of about 10 nm is produced. This arrangement is only conditionally suitable for spectroscopy. However, its use in an imaging system is advantageous, since the signal is still relatively large per detection channel because of the relatively broad detected spectral band. A shift of the free spectral region can additionally occur by rotation of the grating.

Figure 2:
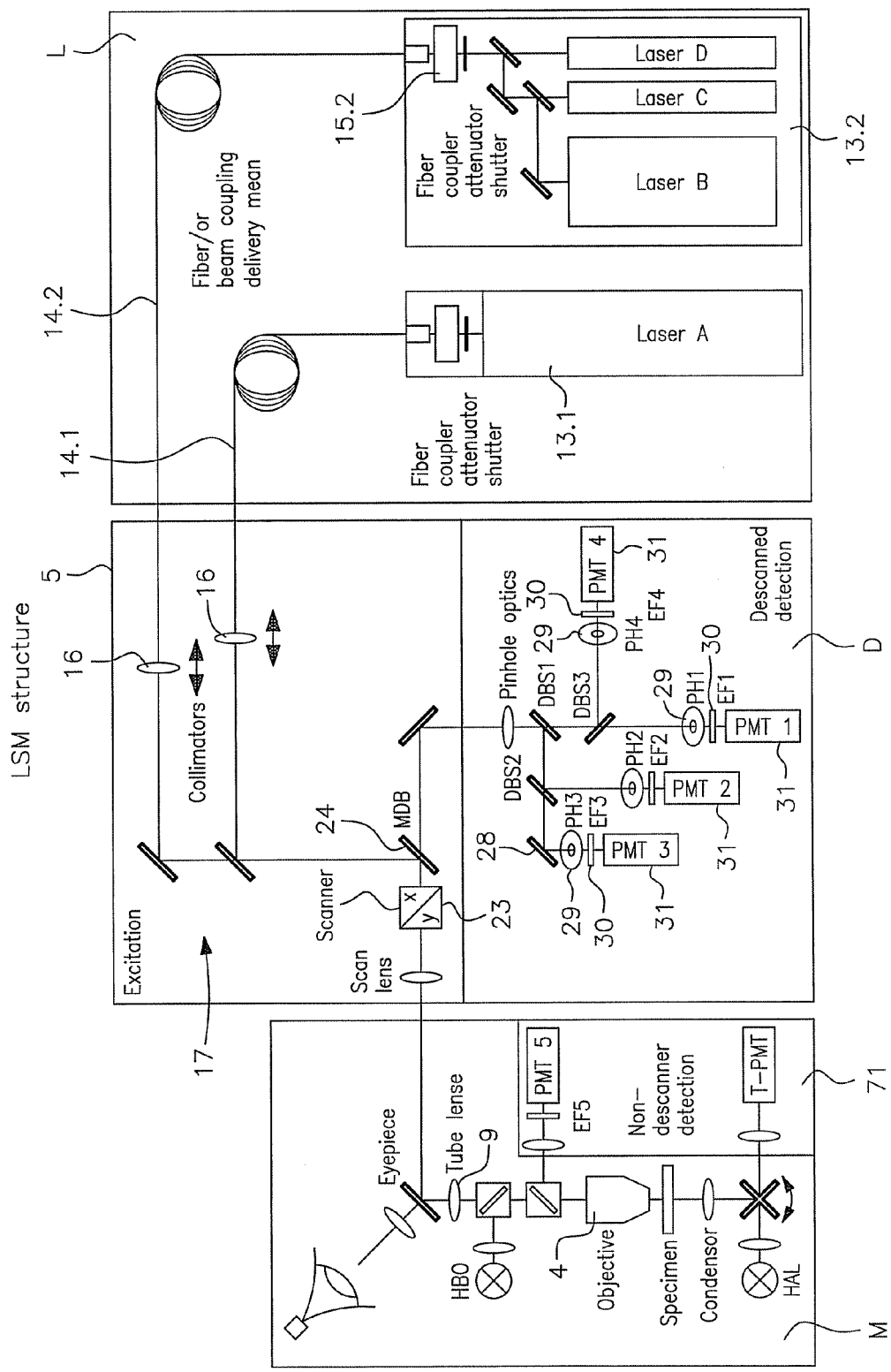
FIG. 2 is a schematic drawing of a laser scan microscope used in practicing the inventive method.
Figure 3:
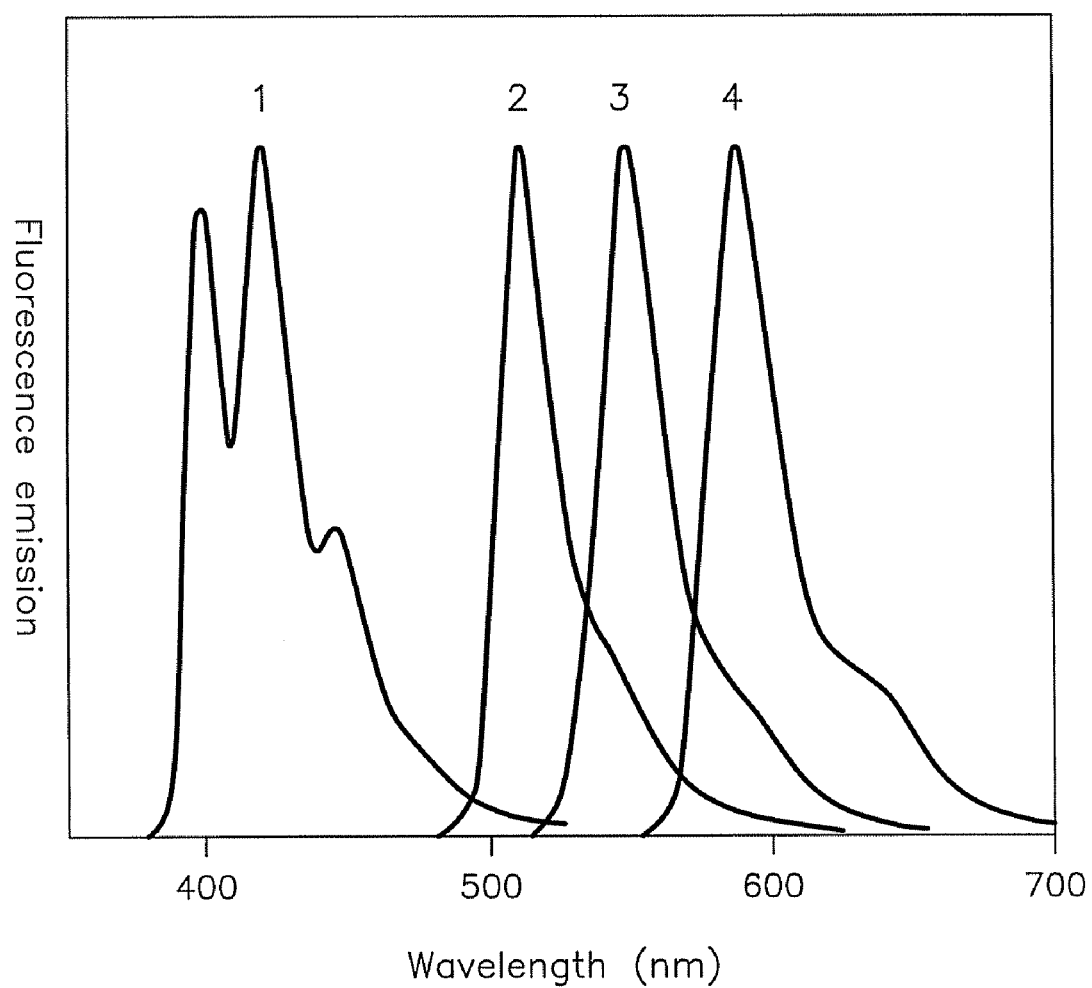
FIG. 3 is a chart showing the emission spectra of several typical dyes.

Another possible variant involves the use of a matrix detector (for example CCD). In this case splitting into different wavelength fractions is carried out in one coordinate by the dispersive element. In the remaining direction, a complete line (or column) of the scanned image is imaged on the matrix detector. This variant is particularly advantageous in constructing a line scanner (lit.: Corle, Kino: "Confocal Scanning Optical Microscopy and Related Imaging Systems," Academic Press, 1996). The essential design corresponds essentially to that of an LSM according to FIG. 2. However, instead of a point focus, a line is imaged in the focus and the sample being investigated is only scanned in one direction. A slit diaphragm instead of a perforated diaphragm serves as confocal diaphragm in such a structure. A nondescanned detection during use of multiphoton absorption can also occur with this arrangement. The confocal diaphragm can again drop out for this purpose.

By spectral splitting of the fluorescence light, after recording of the fluorescence spectra of the fluorescence markers in pure form and recording of the spectra with fluorescence fractions of several markers, a separate recording of the spectral fractions can occur by an unmixing method such as that disclosed in DE 19915137 A1.

It has now been recognized according to the invention that the number of fluorescence markers used for fluorescence marking can be reduced or combinatorics can be utilized, if not only fluorescence spectra are to be used in pure form as reference spectra but also reference spectra of mixed forms are recorded. These mixed forms can be characterized, for example, by the time-dependent color state of the biological material, if a fluorescence marker slowly leads to discoloration. In addition, such mixed states can be characterized by a mixed color if a fluorescence marker changes it color or its excitation properties.

Such mixing conditions can be produced in different ways: they can be present in the sample, be produced by irradiation of the sample, or be the result of a biological process excited by irradiation.

Mixed spectra can characterize a biological process, for example, a concentration change, in which a first spectrum corresponds to a lower concentration state and at least one additional spectrum corresponds to a higher concentration state.

By means of the different reference spectra, image channels are defined and correspondingly evaluated. The generation of such references can occur over the entire image or advantageously over marked "regions of interest" (ROI). A deliberate manipulation by defined irradiation can also occur over such ROI. A reference can also be determined in a first region and deliberate irradiation and measurement can occur in an additional region by extraction of mixed spectra. Demixing and depiction of the spectra can occur after imaging recording or during imaging recording.

It was surprisingly found that new markers like the fluorescing protein Kaede, which turns from green to red during irradiation (lit.: Ando, R., Harna, H., Yamamoto-Hino, M., Mizuno, H. and Miyawaki, A. (2002), An optical marker based on the UV-induced green-to-red photoconversion of a fluorescent protein, PNAS 99/20, 12651-12656) during recording of organic processes, for example inter- and intracellular processes can be used for marking of individual cells or cell populations and spectrally detected. Photoconvertible dyes that change their spectra dynamically based on intracellular processes or dyes that are used for FRET, but also other indicator dyes can be advantageously used by the method according to the invention.

For example, different cells or cell groups in a cell population that has been marked with the dye Kaede can be exposed and converted for different lengths of time with UV or violet light. Different color mixing ratios are then established that are recorded as reference spectra. Different cell populations can then be individually recorded over time. This is true not only for cell cultures, but can also concern both subcellular structures and also entire organisms, in which a certain cell population is irradiated and can be observed in its development, in which the resulting reference can be assigned to specific image channels and can therefore be followed.

A corresponding region can be selected over the ROI. An analysis of transport processes on the cellular and subcellular level can occur. Advantageously, still only one dye is used, which is placed in different states via radiation of other effects that are clearly identifiable by reference formation.

A different rise in fluorescence intensity, as during PA-GFP (photoactivatable GFP, lit.: Patterson, G. H. and Lippincott-Schwartz, J. (2002), A photoactivatable GFP for selective photobleaching of proteins and cells, Science 297, 1873-1877) after excitation with violet light can serve as reference. In the Zeiss LSM META ROIs can be interactively defined directly in the image. The selected laser is switched on and off with pixel precision at the boundary of these regions.

In time series dialog, the start and end of the time series as well as intervals and delays between recordings are fixed. The irradiation parameters that lead to a change in dye properties by photoactivation or photoconversion, for example, repetition rate, wavelength, intensity, position can be automatically incorporated. Evaluation can occur after the experiment or on-line during recording in order to be able to intervene directly in the course of the experiment. The average intensities of ROI in time, as well as the times of photoactivations and conversions are indicated.

The META detector permits the entire spectrum of emission, for example of Kaede, to be recorded and to separate the corresponding mixed forms spectrally during measurement and to display the demixed channels.

Figure 4:
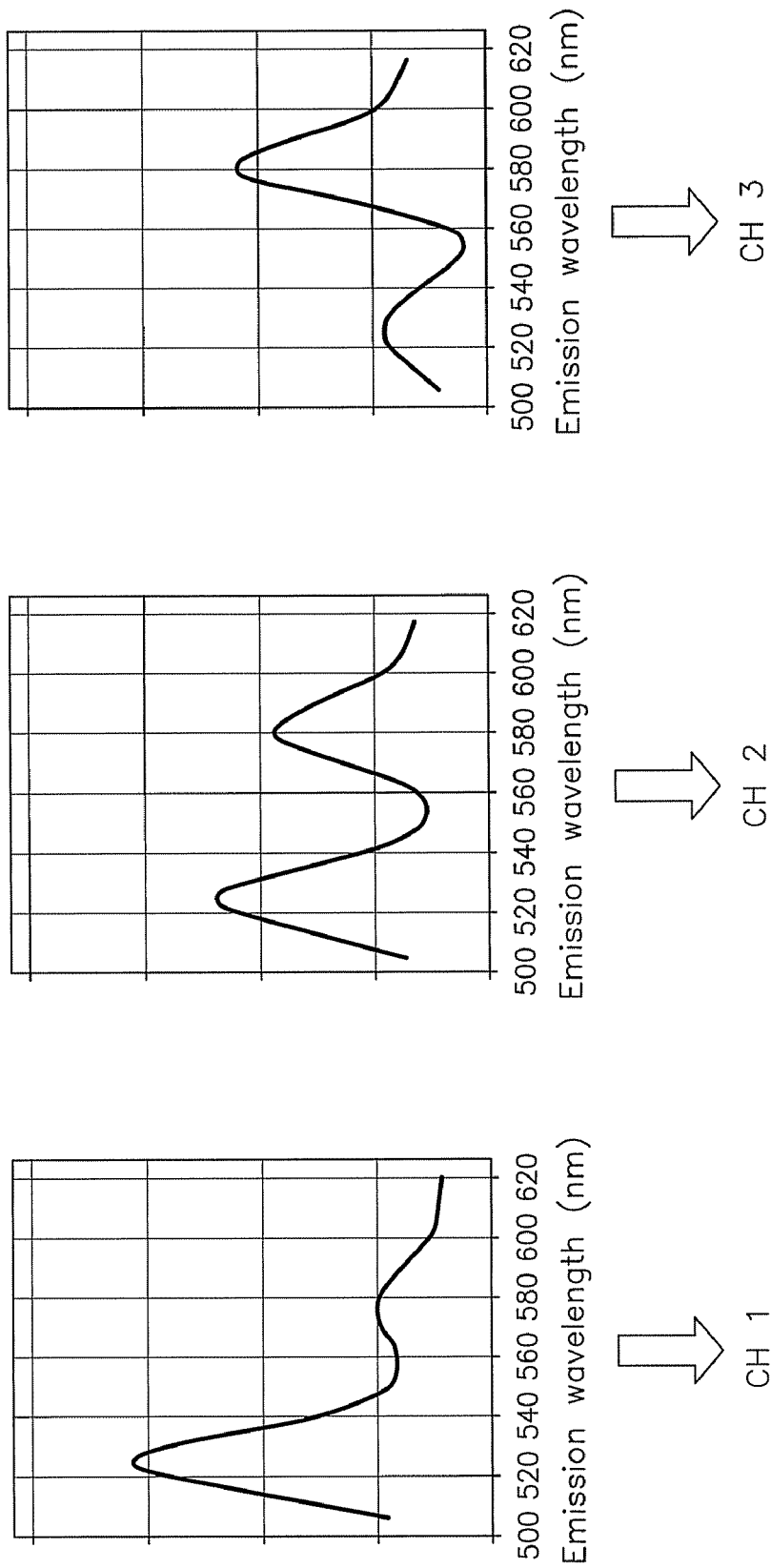
FIG. 4 schematically depicts how different image channels are formed.

FIG. 4 schematically depicts how different image channels CH1-CH3 are formed, in which as shown, different spectral mixed distribution of CH1-3 are used as reference and referred to for image evaluation.

It is to be understood that the present invention is not limited to the illustrated embodiments described herein. Modifications and variations of above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. A method using fluorescence microscopy for image evaluation, the method comprising the steps of:
   using a laser scanning microscope in which an at least partially spectrally resolved detection of the fluorescence spectrum occurs;
   using reference spectra for spectral demixing;
   employing temporally and/or spectrally variable dyes and/or dye combinations for recording of the reference spectra; and
   demixing the recorded reference spectra for image evaluation.

2. The method according to claim 1 wherein the method records organic processes.

3. The method according to claim 1 wherein the method records intracellular processes.

4. The method according to claim 2 wherein the method records intercellular processes.

5. The method according to claim 1 wherein the method records cells and/or cell populations.

6. The method according to one claim 1 in which recording of reference spectra of photoconvertible dyes occurs.

7. The method according to one claim 1 in which recording of reference spectra of photoactivatable dyes occurs.

8. The method according to claim 1 in which recording of reference spectra of indicator dyes occurs.

9. The method according to claim 1 in which recording of reference spectra of dyes occurs that change their spectra dynamically based on intracellular processes.

10. The method according to one claim 1 in which recording of reference spectra of dyes occurs with a different rise in fluorescence intensity.

11. The method according to claim 1 in which recording of reference spectra of the fluorescing protein Kaede occurs.

12. The method according to one claim 1 in which recording of reference spectra of PA-GFP occurs.

* * * * *

UNITED STATES PATENT AND TRADEMARK OFFICE
CERTIFICATE OF CORRECTION

PATENT NO. : 7,688,442 B2  Page 1 of 1
APPLICATION NO. : 10/560426
DATED : March 30, 2010
INVENTOR(S) : Wolleschensky et al.

It is certified that error appears in the above-identified patent and that said Letters Patent is hereby corrected as shown below:

Title page, item [73] Assignee, change "Microimaging"

to --MicroImaging--

Title page, item [30] Foreign Application Priority Data, change "Jul. 16, 2003"

to --June 16, 2003--

Signed and Sealed this

Tenth Day of August, 2010

David J. Kappos
*Director of the United States Patent and Trademark Office*